United States Patent
Günther

(10) Patent No.: US 8,500,864 B2
(45) Date of Patent: Aug. 6, 2013

(54) METHOD AND PLANT FOR TREATING CRUDE GAS, IN PARTICULAR BIOGAS, CONTAINING METHANE AND CARBON DIOXIDE IN ORDER TO PRODUCE METHANE

(75) Inventor: Lothar Günther, Geretsried (DE)

(73) Assignee: MT-Biomethan GmbH, Zeven (DE)

( * ) Notice: Subject to any disclaimer, the term of this patent is extended or adjusted under 35 U.S.C. 154(b) by 1041 days.

(21) Appl. No.: 12/524,661

(22) PCT Filed: Jan. 25, 2008

(86) PCT No.: PCT/EP2008/000561
§ 371 (c)(1),
(2), (4) Date: Jul. 27, 2009

(87) PCT Pub. No.: WO2008/092604
PCT Pub. Date: Aug. 7, 2008

(65) Prior Publication Data
US 2010/0036187 A1   Feb. 11, 2010

(30) Foreign Application Priority Data

Jan. 30, 2007   (EP) .................................. 07001956

(51) Int. Cl.
*B01D 53/00* (2006.01)
*C07C 7/11* (2006.01)

(52) U.S. Cl.
USPC .............................. 95/173; 95/174; 423/228

(58) Field of Classification Search
USPC .......... 95/172–174, 203, 236, 247, 248–250; 423/228, 229; 585/800, 833, 834
See application file for complete search history.

(56) References Cited

U.S. PATENT DOCUMENTS

| 4,971,607 | A  | * | 11/1990 | Gazzi et al. ..................... 95/174 |
| 5,061,465 | A  | * | 10/1991 | Carter ........................... 423/229 |
| 6,168,768 | B1 | * | 1/2001  | Alexion et al. ............... 423/210 |
| 7,192,468 | B2 | * | 3/2007  | Mak et al. ....................... 95/160 |
| 7,604,684 | B2 | * | 10/2009 | Menzel ........................... 95/173 |
| 7,699,914 | B1 | * | 4/2010  | Morrow et al. .................. 96/234 |
| 7,935,178 | B2 | * | 5/2011  | Lechnick et al. ................ 95/172 |
| 2005/0132883 | A1 | * | 6/2005 | Su et al. .......................... 95/235 |
| 2010/0282074 | A1 | * | 11/2010 | Gunther ............................. 95/9 |

FOREIGN PATENT DOCUMENTS

| DE | 102005051952 | B3 | 12/2006 |
| GB | 2017524 | A | 10/1979 |

* cited by examiner

*Primary Examiner* — Frank Lawrence, Jr.
(74) *Attorney, Agent, or Firm* — Laurence A. Greenberg; Werner H. Stemer; Ralph E. Locher

(57) ABSTRACT

A method for treating crude gas, in particular biogas, containing methane and carbon dioxide, in order to produce methane, and a plant suitable for carrying out the method. The method includes (a) washing the crude gas with an amine-containing washing solution, thereby forming a pure gas stream of methane and water, from which water is separated by subsequent cooling and condensation; (b) compressing and heating the washing solution containing $CO_2$ and sulfur compounds and expanding the washing solution in a first expansion stage, during a secondary reaction time of 280 to 1200 seconds and at a constant reaction temperature; (c) cooling the purified washing solution and expanding it in a second expansion stage to normal pressure, whereupon any residual amounts of soluble $CO_2$ and sulfur compounds are separated and the completely purified washing solution is cooled to normal temperature and returned to the washing stage.

11 Claims, 1 Drawing Sheet

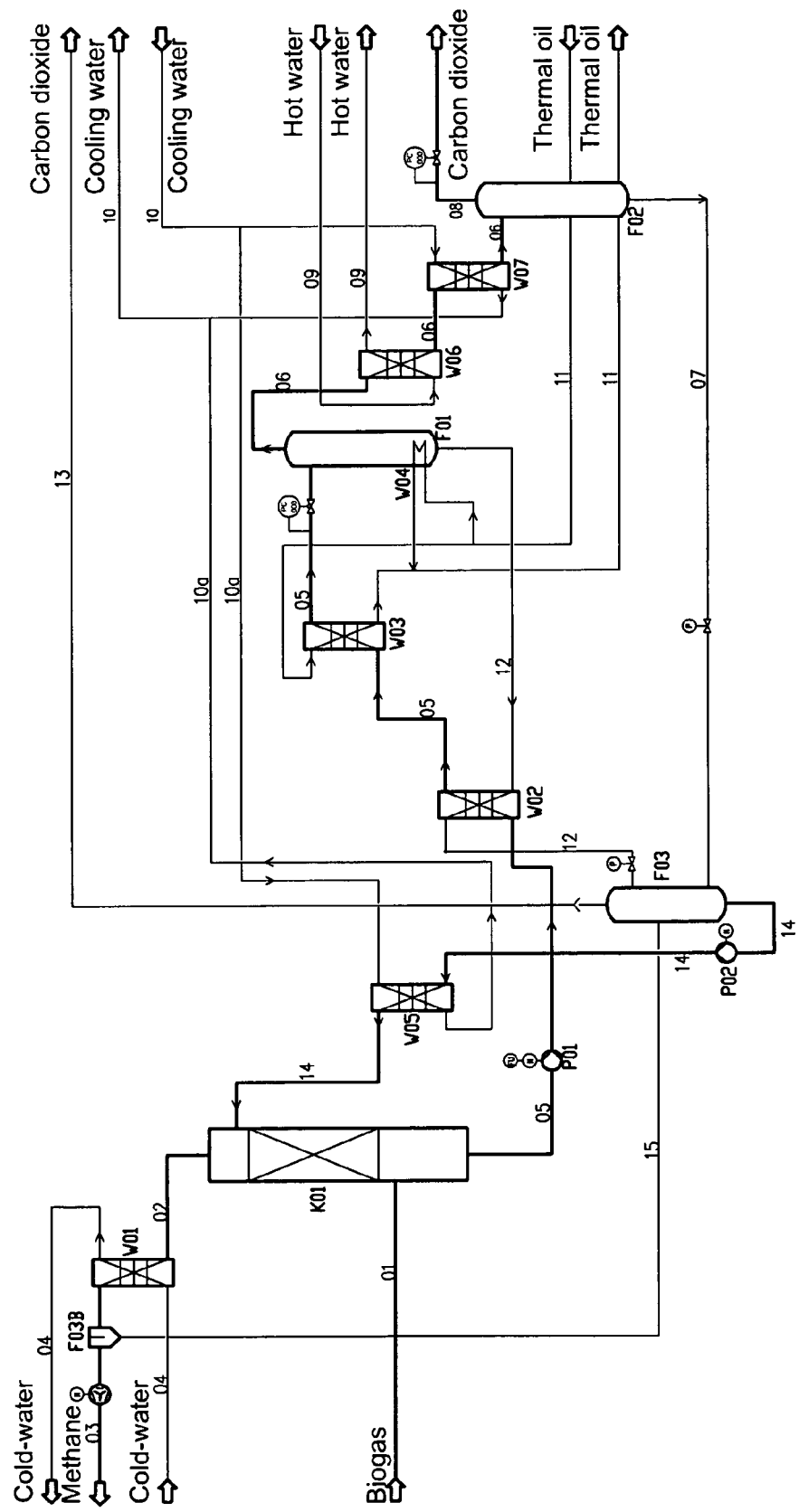

METHOD AND PLANT FOR TREATING CRUDE GAS, IN PARTICULAR BIOGAS, CONTAINING METHANE AND CARBON DIOXIDE IN ORDER TO PRODUCE METHANE

BACKGROUND OF THE INVENTION

Field of the Invention

The invention relates to a method of treating crude gases, in particular biogas, containing methane and carbon dioxide in order to produce methane, and to a plant suitable for carrying out the method.

Biogas is formed by the anaerobic (oxygen-free) fermentation of organic material and is used as a renewable energy source. The gases produced are classified as sewage gas, landfill gas and biogas, depending on the raw materials used, comprising raw materials containing biomass, farmyard manure such as slurry and dung and renewable raw materials.

Methane-containing gases are also produced industrially by thermochemical processes such as gasification.

The refinery gas formed in the distillation of crude oil also contains methane.

The aforementioned gases also contain carbon dioxide and hydrogen sulphide as well as small residual amounts of other chemical substances.

A process is known from DE 10 200 051 952 B3 for producing methane and liquid carbon dioxide from refinery gas and/or biogas. The crude gas is purified in a preliminary stage (removal of impurities such as $NH_3$, $H_2SO_4$, $H_2S$, $SO_2$ and COS) and subsequently conveyed to an absorption column in which the carbon dioxide contained in the crude gas is bound in the scrubbing solution at a pressure preferably of 5 to 30 bar using an amine-containing scrubbing solution. The resulting purified gas contains approximately 98% methane by volume and can be utilised immediately for other purposes. The contaminated scrubbing solution is regeneratively processed by a stripping column under pressure and at increased temperatures (180 to 230° C.).

The disadvantages of this method are that the crude gas must undergo preliminary purification, the methane contained is only up to 98% pure and the regeneration of the scrubbing solution requires a high energy input. Moreover, the process of carrying out the amine scrubbing of the crude gas under increased pressure involves a high level of expenditure on apparatus.

BRIEF SUMMARY OF THE INVENTION

The aim of the invention is to devise a method of treating crude gases, in particular biogas, containing methane and carbon dioxide that will produce methane more economically and with an increased purity of over 99.5% by volume, while at the same time significantly reducing the energy expenditure required for the regeneration of the scrubbing solution. In addition, a plant suitable for carrying out the method is to be devised.

The aim is achieved in accordance with the invention as claimed.

In accordance with the proposed method, the crude gas, preferably biogas, under standard pressure or slight negative pressure (up to 50 mbar), preferably −20 (negative pressure) up to 150 mbar, undergoes a single or multi-stage scrubbing process with an amine-containing scrubbing solution with an amine concentration of at least 15% at standard temperature or temperatures up to 100° C., preferably 20 to 60° C. The water is removed from the pure gas stream of methane and water forming in the scrubbing stage by subsequent cooling and condensation and is, if necessary, returned to the scrubbing circulation.

The scrubbing solution is circulated in the circuit and undergoes a special regenerative processing which results in a scrubbing solution with a particularly high degree of purity.

In this process the scrubbing solution removed from the scrubbing stage and contaminated by $CO_2$ and sulphur compounds is compressed to a reaction pressure of at least 4 bar, preferably 8 to 12 bar, and heated to a temperature above 120° C. Said scrubbing solution is then expanded in an initial expansion stage to a pressure 1 to 3 bar below the reaction pressure. By maintaining a secondary reaction time of 280 to 1,200 seconds and a constant reaction temperature, most of the proportion of $CO_2$ and sulphur compounds is removed from the scrubbing solution as a gas stream. In this initial expansion stage chemically bound $CO_2$ is dissolved in the fluid phase and escapes. The resulting purified scrubbing solution is cooled to temperatures below 50° C. and expanded in a second expansion stage to standard pressure. Residual amounts of soluble $CO_2$ and sulphur compounds still present can therefore be removed in this second expansion stage. In the second expansion stage under the conditions obtaining (temperature and pressure) there is a resolution of the $CO_2$ still physically bound which escapes from the scrubbing solution. From this point the scrubbing solution is of the maximum possible degree of purity. The completely purified scrubbing solution is then cooled to standard temperature and returned to the scrubbing stage for the removal of the methane from the biogas.

Because of the required mode of operation of the circulation of the scrubbing solution, the methane removed in the scrubbing stage can be obtained with a purity of at least 99.5% only if the scrubbing solution is of a correspondingly high degree of purity.

The proposed method makes it possible for the first time to obtain methane of such high purity from biogas.

With a multi-stage removal of methane using amine scrubbing, more than 50% of the total amount of scrubbing solution required should be used in the initial stage. It is advisable to combine the scrubbing solutions from the individual scrubbing stages before the regenerative processing.

It is advantageous to heat the scrubbing solution to the required reaction temperature in two stages, using indirectly heated heat exchangers. In this process the hot scrubbing solution removed from the initial expansion stage can be used as a heat carrier for at least one of the heat exchangers. Depending on its temperature, the scrubbing solution is preferably used as a heat carrier for the first heat exchanger since this has the advantage that the scrubbing solution can be simultaneously cooled in the process to the required temperature of at least 50° C. This has great advantages in terms of the economic use of energy for operating the process. In the initial expansion stage over 95% of the proportions of $CO_2$ and sulphur compounds bound in the scrubbing solution can be removed.

The gas stream removed in the initial expansion stage and containing $CO_2$ and sulphur compounds is conducted through two heat exchangers connected in series and cooled to standard temperature. The water used in the first heat exchanger as a heat carrier is heated to a significantly higher temperature in the process and the hot water produced thereby can be used for other purposes. In this way approximately 60% of the thermal energy supplied immediately before the initial expansion stage can be recovered.

After the gas stream has been cooled, water is removed from it in a downstream separator and the water is returned to the circulation of the scrubbing solution by being conveyed into the separator of the second expansion stage. The water-free gas stream ($CO_2$ and sulphur compounds) is discharged under controlled pressure to the surroundings for example. If the sulphur content of the gas stream is too high, it is desulphurised in a downstream desulphurisation plant.

The reaction times in the initial expansion stage can be further reduced by subjecting the scrubbing solution to ultrasonic treatment. The dwell time in this stage can be reduced by up to approximately 30% with the same removal performance.

A plant suitable for carrying out the method consists of a single or multi-stage scrubbing column for separating methane from the crude gas to be treated. Said column is connected to a circulation line for the scrubbing solution. An initial circulation pump, at least one heat exchanger downstream for heating the scrubbing solution, followed by an initial and a second expansion device are integrated into this circulation line in the direction of flow of the scrubbing solution. The second expansion device downstream serves to remove residual amounts of $CO_2$ and sulphur compounds still present in the scrubbing solution. A second circulation pump and a heat exchanger for cooling the scrubbing solution to standard temperature are integrated into the line for the purified scrubbing solution branching off from this expansion device. After exiting this heat exchanger, the highly pure scrubbing solution is returned to the scrubbing column.

It has proved advantageous to heat the scrubbing solution to the required temperature by two heat exchangers connected in series before it is introduced into the initial expansion stage. The two expansion devices are connected to gas flow lines for removing the $CO_2$ and sulphur compounds. The gas flow line of the initial expansion device is connected to a separator, with two heat exchangers for cooling the gas flow connected in series interposed between said expansion device and the separator. The separator is connected to a line for removing the gas flow and to a line for conveying the removed condensed water into the second expansion device.

At least one of the upstream heat exchangers is integrated into the line for the scrubbing solution branching off from the initial expansion device, with the scrubbing solution flowing through said heat exchanger as a heat carrier and cooled simultaneously in the process. If necessary, the gas flow lines carrying off gases containing sulphur can be connected to a desulphurisation plant. A heat exchanger for condensing the water contained in the methane and a water separator downstream of said heat exchanger for dehumidifying the methane gas should preferably be integrated into the methane gas line connected to the head of the scrubbing column. The water separator is connected via a line to the second expansion device for recirculating the removed water.

The proposed plant can be used for a wide range of outputs and has a high degree of energy efficiency.

BRIEF DESCRIPTION OF THE DRAWING

The invention is now to be explained by an execution example. The associated drawing shows the flow chart for a plant for treating biogas.

DESCRIPTION OF THE INVENTION

The plant shown consists of a single or multi-stage scrubbing column K01. The scrubbing column K01 shown in the drawing is a single stage scrubbing column.

The scrubbing column K01 is connected to a line 01 for feeding in the biogas. A line 02 is provided in the upper part of the scrubbing column K01 for carrying off the methane which contains the water removed in the scrubbing column K01. The water contained in the methane condenses in a downstream heat exchanger W01. The methane from which the water has been removed is drawn off via a line 03. A water separator F03B for dehumidifying the methane is integrated into the line 03. The water removed is conducted via a line 15 into the second expansion device F03. The heat exchanger W01 is fed via a circulation line 04 with cold water, which is cooled in a cooling device which is not shown in greater detail.

On the base of the scrubbing column K01, a scrubbing solution in which $CO_2$ and sulphur compounds are bound is pumped by a circulation pump P01 via a line 05 to an initial heat exchanger W02, from where it is pumped to a second heat exchanger W03 and from that to an initial expansion device F01 in which the major proportions of the $CO_2$ and sulphur compounds are removed from the scrubbing solution by a flash expansion. A heat exchanger W04 is integrated into the flash expansion device F01 to maintain the required reaction temperature.

$CO_2$ and sulphur compounds are drawn off at the head of the flash expansion device F01 via the line 06 and conducted for further cooling through a third and fourth heat exchanger W06 and W07. The condensed water is led off in a downstream separator F02 via the line 07 and the $CO_2$ and sulphur compounds are discharged under controlled pressure to the surroundings via the line 08. The heat exchanger W06 is fed with hot water via a circulation line 09 and the heat exchanger 07 is fed with cold water via a circulation line 10. Thermal oil is fed to and removed from the heat exchanger W03 via a circulation line 11. The heat of condensation released during the flash expansion is used to heat the heat exchanger W06. Approximately 60% of the thermal energy supplied in the heat exchanger W03 can therefore be recovered as hot water which can be used for other purposes.

The hot purified scrubbing solution is conducted via a line 12 from the flash expansion device F01 as a heat carrier to the heat exchanger W02 from where it is conveyed under controlled pressure to a second expansion device, the separator F03. The condensation water accumulating in the separator F02 is fed under controlled pressure to the separator F03 via the line 07. The $CO_2$ and sulphur compounds still contained in the scrubbing solution and/or condensation water are removed in said separator and discharged to the surroundings via the line 13. The scrubbing solution accumulating in the separator F03 is pumped by the circulation pump P02 via the line 14 to the heat exchanger W05 and returned after cooling to the scrubbing column K01. The heat exchanger W05 is integrated into the circulation line 10 via the lines 10a for cooling the said heat exchanger. The plant described makes it possible to treat biogas in an extremely economic and energy-saving manner.

The method of operation of the plant is explained below.

In the course of biogas production, the biogas formed undergoes preliminary desulphurisation, with other components that can interfere with the process being removed without feeding in oxygen or air. A typical example of the composition of conventional biogas is as follows:

| | |
|---|---|
| Methane | 52% by volume |
| Carbon dioxide | 44% by volume |
| Water | 3% by volume |
| Hydrogen | 0.1% by volume |
| Sulphur compounds | 0.2% by volume as $H_2S$ and COS (organic sulphur compounds) or traces of sulphur compounds, ammonia in the region of under 2 ppm. |

The biogas to be treated (500 $Nm^3/h$; N=standard condition) is fed in directly to the scrubbing column K01 (without additional preliminary purification) under the given conditions at a temperature of 20 to 60° C. The scrubbing process for removing $CO_2$, $H_2S$ and COS from the biogas is carried out in said column under standard pressure or a slight vacuum (−10 to 150 mbar). Scrubbing is carried using a scrubbing solution containing at least one amine component, preferably diethanolamine at a concentration of 15 to 50%. The amount of scrubbing solution used depends on the amine concentration, with the proportion of water being at least 20%. Where a scrubbing solution with an amine concentration of 20% is used for purifying 500 $Nm^3/h$ of biogas, approximately 15 $m^3/h$ of scrubbing solution is required. Where a scrubbing solution with an amine content of 30% is used, the amount required is 9 $m^3/h$. The sulphur compounds and $CO_2$ contained in the biogas are completely bound with the scrubbing solution on being brought into contact with said scrubbing solution. The purified biogas exiting the scrubbing column K01 via the line 02 consists of methane and water with a very small residual proportion (0.2% or less) of $CO_2$. The water contained in the methane condenses in a downstream cooling stage (heat exchanger W01). The condensed water is returned to the scrubbing circulation and therefore the proportion of water in the scrubbing circulation is maintained at the same level. The methane, which is still wet, is dehumidified in a water separator F03B and the water removed is returned via the line 15 to the second expansion device F03.

The methane removed has a purity of over 99.5% by volume. This can be increased to almost 100% purity by additional drying.

The scrubbing solution accumulating on the base of the scrubbing column K01 (approximately 15 $m^3/h$, amine concentration 20%), compressed to a pressure of approximately 8.5 bar, is conducted by the circulation pump P01 to an initial heat exchanger W02 and heated in said heat exchanger by indirect heat exchange to a temperature of approximately 145° C. The purified scrubbing solution formed after the flash expansion F01 is used as a heat exchanger medium. The scrubbing solution removed from the heat exchanger W02 is then heated in a second heat exchanger W03 to a temperature of approximately 165° C. An external heat carrier, e.g. thermal oil, flows through the heat exchanger W03.

The scrubbing solution is then expanded to a pressure of approximately 6.5 bar in an initial expansion stage, the flash expansion device F01. In this process, the proportion of chemically bound carbon dioxide and sulphur compounds in the scrubbing water is reduced to 1/10 during a secondary reaction time of 480 seconds and a reaction temperature of approximately 165° C. The proportion of chemically bound $CO_2$ and sulphur is reduced under these conditions from 45 g/l to 5 g/l.

Under other process conditions the secondary reaction time can also amount to 280 seconds to 1200 seconds, with short secondary reaction times being advantageous in terms of the economic operation of the process. The reaction temperature is maintained by a heat exchanger W04 integrated into the flash expansion device F01. The flash expansion should preferably take place at a flash temperature 1 to 10° C. below the evaporating temperature of water, at an expansion of approximately 8.5 bar to approximately 6.5 bar and a temperature of approximately 165° C. The purified scrubbing solution, now containing only small amounts of $CO_2$ and sulphur compounds and at a temperature of approximately 165° C., is fed via the line 12 to the heat exchanger W02 as a heat carrier, being cooled in the process to a temperature of 34° C. The scrubbing solution is then expanded in a second expansion stage (separator F03) to standard pressure. The residual amounts of $CO_2$ and sulphur compounds still contained in the scrubbing solution escape in the process at the head of the separator and can be discharged to the surroundings. The completely purified scrubbing solution is conveyed to the heat exchanger W05 by the circulation pump P02 and cooled to standard temperature in said heat exchanger and then returned to the scrubbing column K01.

In the second expansion stage a resolution occurs of the $CO_2$ still physically bound which escapes via line 13. The second expansion stage F03 produces the maximum possible degree of purity of the scrubbing solution. Since the scrubbing solution is circulated in the circuit and is returned after purification to the scrubbing stage K01, its degree of purity also affects the degree of purity of the methane removed in the scrubbing stage. Methane with a purity of at least 99.5% cannot be obtained from biogas unless the recirculated scrubbing solution is of a high degree of purity.

Approximately 10% of $CO_2$ is still chemically bound in the highly pure scrubbing solution and can be separated only with difficulty and at a level of expenditure that is not economically justifiable. The gas mixture of carbon dioxide, water and sulphur compounds exiting from the head of the flash expansion device F01 is cooled to a temperature of 60° C. in the heat exchanger W06 and to standard temperature (approximately 25° C.) in the downstream heat exchanger W07. The condensed water is then removed in the separator F02. This is conducted in a dosed amount via the line 07 to the separator F03 where it mixes with the completely purified scrubbing solution. The gas mixture ($CO_2$ and sulphur compounds) streaming off at the head of the separator F02 is discharged under controlled pressure to the surroundings.

If there are impermissibly high concentrations of sulphur compounds in the gas mixture removed, an additional downstream desulphurisation is carried out, e.g. by biofilter, adsorption or as physical/chemical or biological scrubbing. The reaction time of the chemical decomposition of the scrubbing solution taking place in the separator F01 can be significantly shortened, by 70% for example, by additional ultrasonic treatment under the same temperature and pressure conditions. As previously explained, the scrubbing stage K01 for removing the methane can be multi-staged, preferably two staged. The scrubbing columns required for this are connected in series. The amount of scrubbing solution used in the initial scrubbing stage should be more than 50% of the overall amount required. The scrubbing solutions accumulating in both scrubbing stages are combined and regeneratively processed as previously described.

Based on an amount of biogas used of 500 $Nm^3/h$ and an amount of scrubbing solution used of 15 $m^3/h$ (amine concentration 20%), 260 $m^3/h$ of methane with a purity of at least 99.5% is obtained under the aforementioned conditions. By using the proposed regenerative processing, the amount of scrubbing solution used can be recovered with a maximum possible degree of purity of almost 100% and recirculated in the circuit.

The invention claimed is:

1. A method of treating crude gases containing methane and carbon dioxide to produce methane, which comprises:
    a) subjecting the crude gas to a single or multi-stage scrubbing process with an amine-containing scrubbing solution at an amine concentration of at least 15% with the formation of a pure gas stream consisting of methane and water, removing the water from the pure gas stream and, optionally, returning the water to a scrubbing circuit by downstream cooling and condensation;
    b) compressing a scrubbing solution containing $CO_2$ and sulfur compounds obtained in step a) to a reaction pressure of at least 4 bar, heating to a temperature above 120° C. and expanding, in an initial expansion stage, to a pressure that is 1 to 3 bar below the reaction pressure, while maintaining a secondary reaction time of 280 to 1200 seconds and a constant reaction temperature, for removing a major proportion of the $CO_2$ and sulfur compounds from the scrubbing solution and drawing off as a gas stream;
    c) cooling the thus purified scrubbing solution to a temperature below 50° C. and expanding in a second expansion stage to standard pressure, to remove residual amounts of soluble $CO_2$ and sulfur compounds still present to form a completely purified scrubbing solution, and cooling the completely purified scrubbing solution to standard temperature and returning to the scrubbing stage.

2. The method according to claim 1, which comprises scrubbing the crude gas at standard pressure or at a slight vacuum up to 50 mbar, and with an amine-containing scrubbing solution at an amine concentration of at least 15% at standard temperature or temperatures up to 100° C.

3. The method according to claim 1, wherein step b) comprises compressing the scrubbing solution to a reaction pressure of between 8 and 12 bar.

4. The method according to claim 1, wherein the multi-stage scrubbing process includes an initial scrubbing stage in which more than 50% of a total amount of scrubbing solution required is used and wherein the scrubbing solutions of the individual scrubbing stages are combined and regeneratively processed.

5. The method according to claim 1, which comprises heating the scrubbing solution obtained after washing to a required reaction temperature in two stages by way of indirectly heated heat exchangers.

6. The method according to claim 1, which comprises conducting the gas stream containing $CO_2$ and sulfur compounds separated in an initial expansion stage through two heat exchangers connected in series and cooling to standard temperature and conveying to a downstream separator for removing water condensed from the gas stream and removing the water-free gas stream under controlled pressure.

7. The method according to claim 1, which comprises using hot scrubbing solution removed from an initial expansion stage as a heat carrier for at least one of the heat exchangers and thereby cooling the scrubbing solution to a temperature of no more than 50° C.

8. The method according to claim 1, which comprises heating the crude gas to a temperature of 20 to 60° C. in process step a) and adjusting to a pressure ranging from −20 to 150 mbar.

9. The method according to claim 1, which comprises removing more than 95% of the proportions of $CO_2$ and sulfur compounds bound in the scrubbing solution during the initial expansion stage.

10. The method according to claim 1, which comprises desulfurizing at least the gas stream removed from the initial expansion stage in a downstream desulphurization plant.

11. The method according to claim 1, which comprises subjecting the scrubbing solution to an ultrasonic treatment during the initial expansion phase.

* * * * *